United States Patent
De Graaff et al.

[11] Patent Number: 6,146,594
[45] Date of Patent: Nov. 14, 2000

[54] SYRINGE ARRAY WITH ADJUSTABLE NEEDLE SPACING

[75] Inventors: David De Graaff, Menlo Park; Kevin Heyes, San Lorenzo; David J. Wright, Fremont; Paul B. Robbins, Palo Alto, all of Calif.

[73] Assignee: Robbins Scientific Corporation, Sunnyvale, Calif.

[21] Appl. No.: 09/344,750

[22] Filed: Jun. 25, 1999

Related U.S. Application Data

[60] Provisional application No. 60/119,470, Feb. 10, 1999.

[51] Int. Cl.$^7$ .................................. B01L 3/02; G01N 1/16
[52] U.S. Cl. ........................... 422/100; 422/99; 422/104; 73/863.31; 73/863.32; 73/864.11; 73/864.16; 73/864.17
[58] Field of Search ............................ 422/99, 100, 104; 604/207, 208; 73/863.31, 863.32, 864.11, 864.13, 864.16, 864.17

[56] References Cited

U.S. PATENT DOCUMENTS

| | | | |
|---|---|---|---|
| 3,738,493 | 6/1973 | Cummins et al. | 210/198.3 |
| 4,106,911 | 8/1978 | Marcelli | 422/63 |
| 4,141,833 | 2/1979 | Cummins | 210/198.3 |
| 4,276,048 | 6/1981 | Leaback | 436/180 |
| 4,459,864 | 7/1984 | Cirincione | 73/863.32 |

*Primary Examiner*—Jill Warden
*Assistant Examiner*—Dwayne K. Handy
*Attorney, Agent, or Firm*—Larry B. Guernsey

[57] ABSTRACT

A syringe array (10) for holding a plurality of syringes (12), each syringe having a barrel (14), a plunger (18) and a needle (16), the syringe array (10) including a distal assembly (50) which holds the plungers (18) of the plurality of syringes (12) and by which all of the plurality of plungers (18) are urged to move in unison, a pivot assembly (52) wherein a portion of each the barrels (14) of the plurality of syringes (12) is pivotally attached to a pivot (92, 94) and a proximal assembly (48) wherein each needle (16) of the plurality of syringes (12) is positioned with a controlled center-to-center spacing (100, 102) from each other. An adjusting portion (62, 64, 70) of the syringe array (10) is adjustable to controllably change the needle center-to-center spacing from a first spacing (100) to at least a second spacing (102) as the barrel portions (14) are allowed to rotate about the pivots (92, 94).

10 Claims, 5 Drawing Sheets

SYRINGE ARRAY WITH ADJUSTABLE NEEDLE SPACING

This application claims priority from U.S. Provisional Application Serial No. 60/119,470, filed Feb. 10, 1999, which has the same inventors as the present application.

TECHNICAL FIELD

The present invention relates generally to multi-channel devices used in collecting, transporting and dispensing laboratory materials, and more particularly to syringe arrays used in loading sequencing gels.

BACKGROUND ART

Syringes have long been used as devices for measuring and dispensing liquids in laboratory and health care situations. Recent developments in laboratory processing have allowed the use of standardized 96 well microplates with 9 mm center-to center spacing, or 384 well microplates with 4.5 mm spacing. The Society of Biomolecular Screening (SBS) has established standard XY dimensions for multi-well microplates. This has allowed many processes to be automated. One such process uses sequencing gels for processing on an automated sequencer. Sequencing gels for automated sequencers are typically 0.2 mm or 0.4 mm thick. They are made of a porous matrix of cross-linked polymers sandwiched between two glass plates. The length and width of the gels can range in size up to approximately 30 cm×40 cm. Syringes are used to dispense samples so that they flow between the glass plates and onto the top of the gel which is about one centimeter below the top edges of the glass plates. The needles are therefore necessarily of a very narrow gauge. It has been found that grouping syringes into arrays is an efficient way to withdraw material from an entire row or column of a micro-well plate and transfer this material either to another micro-well plate or to a sequencing gel.

Sequencing gels can be configured for different numbers of "wells", each of which will hold a different sample. A well is essentially a chamber at the top surface of the gel where the surface of the gel is the well bottom and the sides of the well are formed by two "teeth" of a plastic "comb". A comb is inserted down between the plates until all the teeth contact the top of the gel and form the wells. The tops of the wells are open for samples to enter. Although width of a gel for a given automated sequencer generally stays the same, recently new sequencers have increased the number teeth in a comb, and thus increasing the number of wells present in a given gel. The result is that there are more, narrower wells with decreased center-to-center spacing of the wells. Syringe arrays that are to be used with these newer sequencers have had to deal with the change in center-to-center spacing either by having dedicated syringe arrays with fixed spacing which will accommodate only one such center-to-center spacing, or by attempting to adjust the spacing of the needle to match several different sequencers with different spacings. Prior art syringe arrays with adjustable spacing have provided sliding spreaders at the needle end of the syringes, which bend the needles so that the separation between them matches the center-to-center spacing of the wells. This has obvious disadvantages of causing stress and damage to the needles.

Thus there is a need for a syringe array with adjustable needle spacing which can match a variety of center-to-center spacings of sequencing gel wells without bending the needles of the array.

DISCLOSURE OF INVENTION

Accordingly, it is an object of the present invention to provide a device for collecting, transporting and dispensing multiple samples of material simultaneously.

Another object of the present invention is to provide a multi-syringe device with adjustable needle spacing.

And, another object of the invention is to provide needle spacings for a multiple syringe array which are compatible with standard multi-well center-to-center spacing, but which can expand to a different, larger needle spacing to fit the center-to-center well spacing of new automated gel sequencers.

A further object of the present invention is to provide an adjustable spacing device which does not bend and put stress upon the needles of the array.

Briefly, one preferred embodiment of the present invention is a syringe array for holding a plurality of syringes, each syringe having a barrel, a plunger and a needle. The syringe array includes a distal assembly which holds the plungers of the syringes and by which all of the plungers are urged to move in unison. The syringe array also includes a pivot assembly wherein a portion of each the barrels is pivotally attached to a pivot, and a proximal assembly wherein each needle of the plurality of syringes is positioned with a controlled center-to-center spacing from each other. An adjusting portion of the syringe array is adjustable to controllably change the needle center-to-center spacing from a first spacing to at least a second spacing as the barrel portions are allowed to rotate about the pivots.

An advantage of the present invention is that needle spacing can be easily adjusted.

Another advantage of the present invention is the adjustable spacing can be used when going from a larger spacing to a smaller spacing or from a smaller spacing to a larger.

And, another advantage of the present invention is that it is adjustable to 9 mm needle spacing, which is standard center-to-center spacing for 96 multi-well microplates, and also to 10.8 mm needle spacing for use with newly introduced automated gel sequencers.

A further advantage of the present invention is that there is no bending of the needles, and the accompanying stress on the needles and other components is eliminated.

These and other objects and advantages of the present invention will become clear to those skilled in the art in view of the description of the best presently known mode of carrying out the invention and the industrial applicability of the preferred embodiment as described herein and as illustrated in the several figures of the drawings.

BRIEF DESCRIPTION OF THE DRAWINGS

The purposes and advantages of the present invention will be apparent from the following detailed description in conjunction with the appended drawings in which.

BEST MODE FOR CARRYING OUT THE INVENTION

A preferred embodiment of the present invention is a syringe array with variable needle spacing. As illustrated in the various drawings herein, and particularly in the view of FIG. 1, a form of this preferred embodiment of the inventive device is depicted by the general reference character 10. In all figures, the tip of the needles will be considered to be the proximal end of the device and the handles of the plungers will be at the distal end, and the directions "proximal" and "distal" shall in all cases be relative to these reference points.

Figure 1:
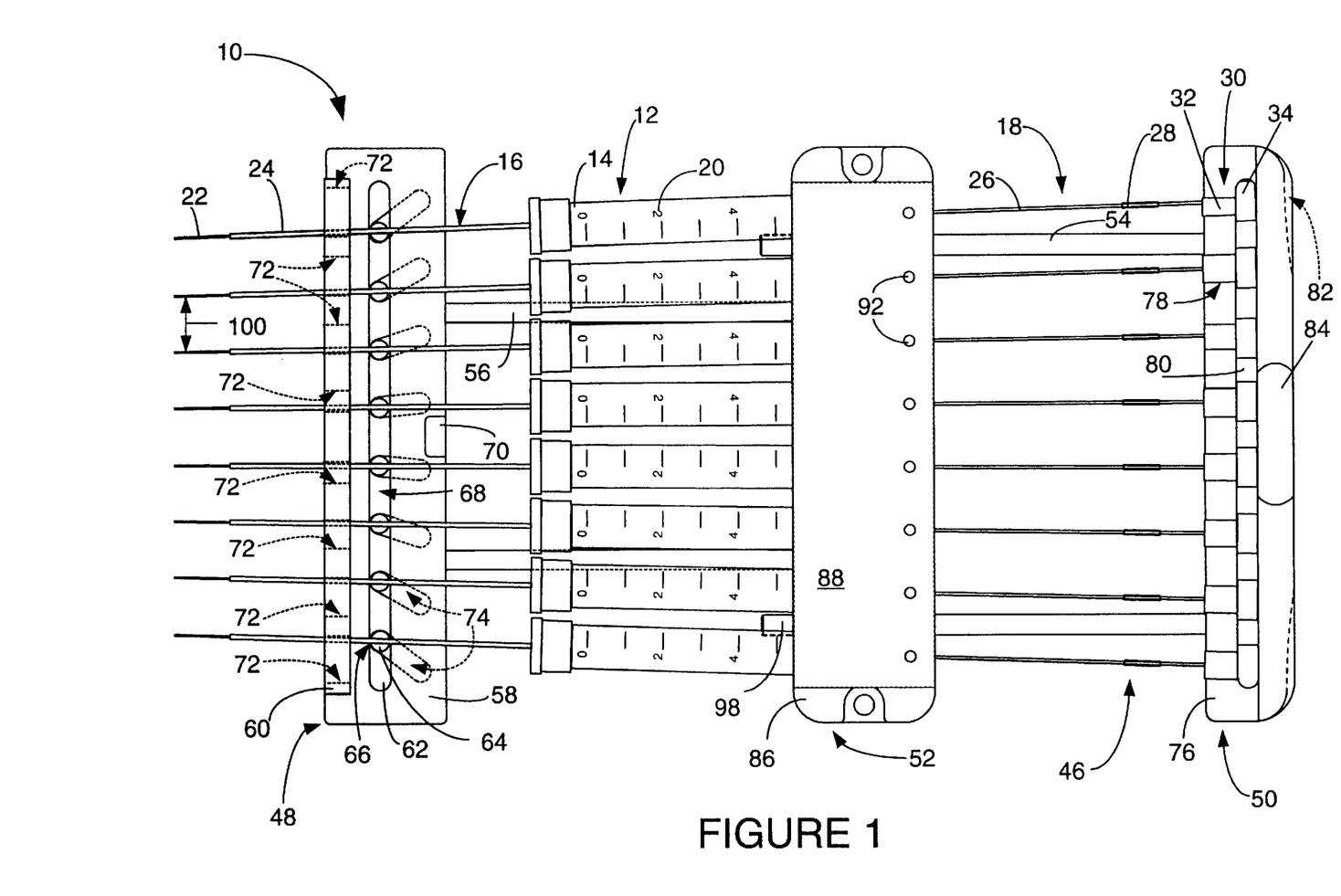
FIG. 1 illustrates a top plan view of the syringe array of the present invention, which is in the closed and dispensing positions.

FIG. 1 illustrates a top plan view of the syringe array with variable needle spacing 10. In the preferred embodiment, the array holds 8 syringes 12, although greater or lesser numbers of syringes are also contemplated by this invention as well. Eight syringes 12 have been used in this embodiment because of the ease of use with standard multi-well microplates, which conventionally have 96 wells in an 8×12 configuration. The syringes 12 are also preferably of the type having replaceable needles as shown in Applicant's co-pending application Ser. No. 60/089,422, but the syringe array 10 is meant to work with any standard syringe. Also as described in Applicant's co-pending application, the currently preferred replaceable needle assemblies have "two-stage needles" in which an inner member of highly flexible or "superelastic" material such as binary nickel-titanium alloy is joined to a sheath of more rigid material. This allows for sufficient rigidity that precise placement of the needle tip is facilitated, but allows some flexibility at or near the needle tip in order to minimize damage to the tip and ease directing the needle tips into very narrow channels. Such superelastic material for the inner member is available as "Alloy BB" from Memry Corporation.

Syringe arrays of different sizes are contemplated to accommodate syringes of different sizes and capacities, as well as different needle spacings and ranges of adjustment for the needle spacings.

Figure 2:
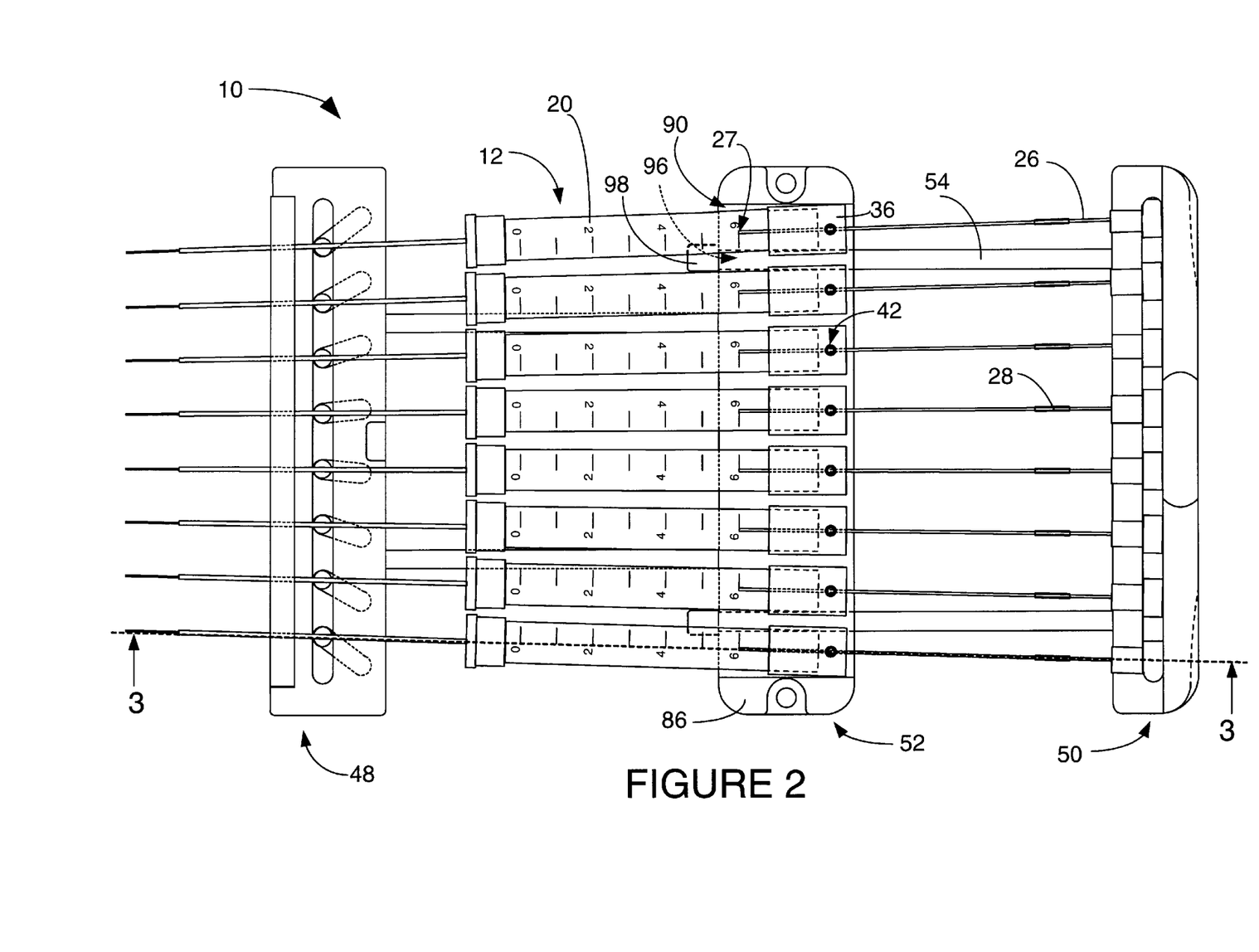
FIG. 2 shows a top plan view of the syringe array of the present invention, which is in the closed and dispensing positions with the top cover of the pivot assembly removed.

Each syringe 12 is an assembly having a barrel 14, a needle assembly 16, a plunger assembly 18, and volumetric markings 20. The needle assembly 16 is in turn made up of an inner member 22 and a sheath 24. Referring now also to FIG. 2, the plunger assembly 18 also includes a plunger 26 with a tip 27, an enlarged plunger portion 28, a handle 30 with a shaft 32 and enlarged handle end 34 and a plunger cap 36. The plunger cap 36 has an upper pivot hole 42 and lower pivot hole 44.

Especially when removable needle syringes are used, the barrel can optionally include an enlarged internal diameter portion with a plunger stop which can prevent the plunger tip from traveling too far in the proximal direction and dislodging the needle assembly. Alternately, the plunger enlarged portion can be made of larger diameter than the inner bore of the barrel to limit the travel of the plunger tip. The barrel may also have a conical lead-in portion so that the plunger tip can be easily inserted into the barrel with out damage.

The syringe array 10 support structure 46 includes a proximal assembly 48, a distal assembly 50 and a pivot assembly 52, as well as slide rods 54 and stationary rods 56.

The proximal assembly 48 includes a proximal housing 58, a footplate 60, a slot plate 62, a guide pin retainer 63 (see FIG. 4), and a number of guide pins 64, one for each syringe 12 in the array 10, each guide pin having a needle slot 66. The proximal housing 58 has a transverse slot 68 and a control tab 70. The footplate 60 also has a series of footplate transverse slots 72 (see also FIG. 4). The guide pins 64 are made to travel in guide slots 74, which are shown in dashed lines in FIG. 1.

The distal assembly 50 includes a distal housing 76 having a number of handle slots 78 and a transverse handle slot 80. There are also optional finger grooves 82 and cut away 84.

The pivot assembly 52 includes a pivot housing 86 with a top cover 88 and a housing cavity 90 (see FIG. 2) into which the syringe barrels 14 and plunger caps 36 fit. The top cover 88 is provided with a number of upper pivot pins 92, which are equal in number to the number of syringes 10. The pivot housing 86 also has lower pivot pins 94 which are equal in number to the syringes 10. The pivot housing 86 additionally has through channels 96 (seen in dashed lines in FIG. 2) through which the slide rods 54 extend. Although the pivot assembly 52 is pictured as being at the distal end of the syringe barrel 14, it is perfectly possible that the pivot assembly 52 be located at the proximal end of the syringe barrels 14, or anywhere intermediate to these points.

The stationary rods 56 are rigidly attached at one end to the pivot housing 86 and at the other to the proximal housing 58, thus keeping the pivot assembly 52 and proximal assembly 48 in fixed spatial relation to each other. The slide rods 54 are rigidly fixed at one end to the distal assembly 50 and extend through the channels 96 in the pivot housing 86 and are each clamped with a retaining collar 98. The pivot assembly 52 is thus allowed to travel in the axial direction of the slide rods 54 until stopped by contact with the retaining collars 98, but are prevented from motion in any direction except along the axis of the slide rods 54.

When the syringe array 10 is to be assembled, the top cover 88 of the pivot assembly 52 is removed. A syringe 12 is installed by inserting the needle inner member 22 into the transverse slot 72 of the footplate 60 of the proximal assembly 48. The needle sheath 24 is placed into the needle slot 66 of a guide pin 64. Each guide pin 64 has previously been placed in a guide slot 74, which will control its path of travel. The barrel 14 and plunger cap 36 of the syringe 10 are placed in the housing cavity 90 so that one of the lower pivot pins 94 is inserted into the lower pivot hole 44 of the plunger cap 36. The syringe handle 30 is then inserted into the distal assembly 50 by placing the handle shaft 32 into a handle slot 78 and the enlarged handle end 34 into the transverse handle slot 80. Each syringe 12 is placed into the array 10 until all positions have been filled. The top cover 88 of the pivot assembly 52 is then replaced, so that the upper pivot pins 92 are all inserted into the upper pivot holes 42 of the plunger cap 36. The upper and lower pivot pins 92, 94 form a series of hinge points at which each of the syringes 10 can move.

The spacing between the needles is represented by dimension 100, which in FIG. 1 is minimized, as the syringe array is in "closed position". In this position, the proximal housing 58 is positioned at the far extreme of its travel in the proximal direction, and the guide pins 64 are in the proximal end of the guide slots 74. As the guide slots 74 are angled, the guide pins 64 are not only closest to the proximal end, but are the closest to each other, and consequently the needles 16 are closest to each other, with minimum spacing 100.

FIG. 2 illustrates the syringe array 10 from which the top cover 88 has been removed. The syringes 12 can now be more easily seen in the housing cavity 90. The plunger caps 36 can be seen with the upper pivot holes 42 into which the upper pivot pins (not shown in this view) are inserted. The array in this figure is in "closed position" and also in "dispensing position" in which the plungers are all drawn back by pulling the distal assembly, which has captured the handles of all the syringes, away from the pivot assembly 52. The slide rods 54 travel through the through channels 96 until the retaining collar 98 contacts the pivot housing 86 and prevents further motion in the distal direction. Preferably this point is reached before any of the plungers 26 leave the barrels 14. When material is to be dispensed, the distal assembly 50 is pushed towards the pivot assembly 52, simultaneously pushing all the plungers 26 into the barrels 14 of the syringes 12. This motion continues until the plunger portion 26 reaches the limit of travel in the proximal direction. This position is referred to as the "aspirating position" as the syringe 12 is now ready to draw material into the barrel 14 by aspiration. This position preferably corresponds with the tip 27 of the plunger 26 reaching the zero point of the volumetric markings 20.

Figure 3:
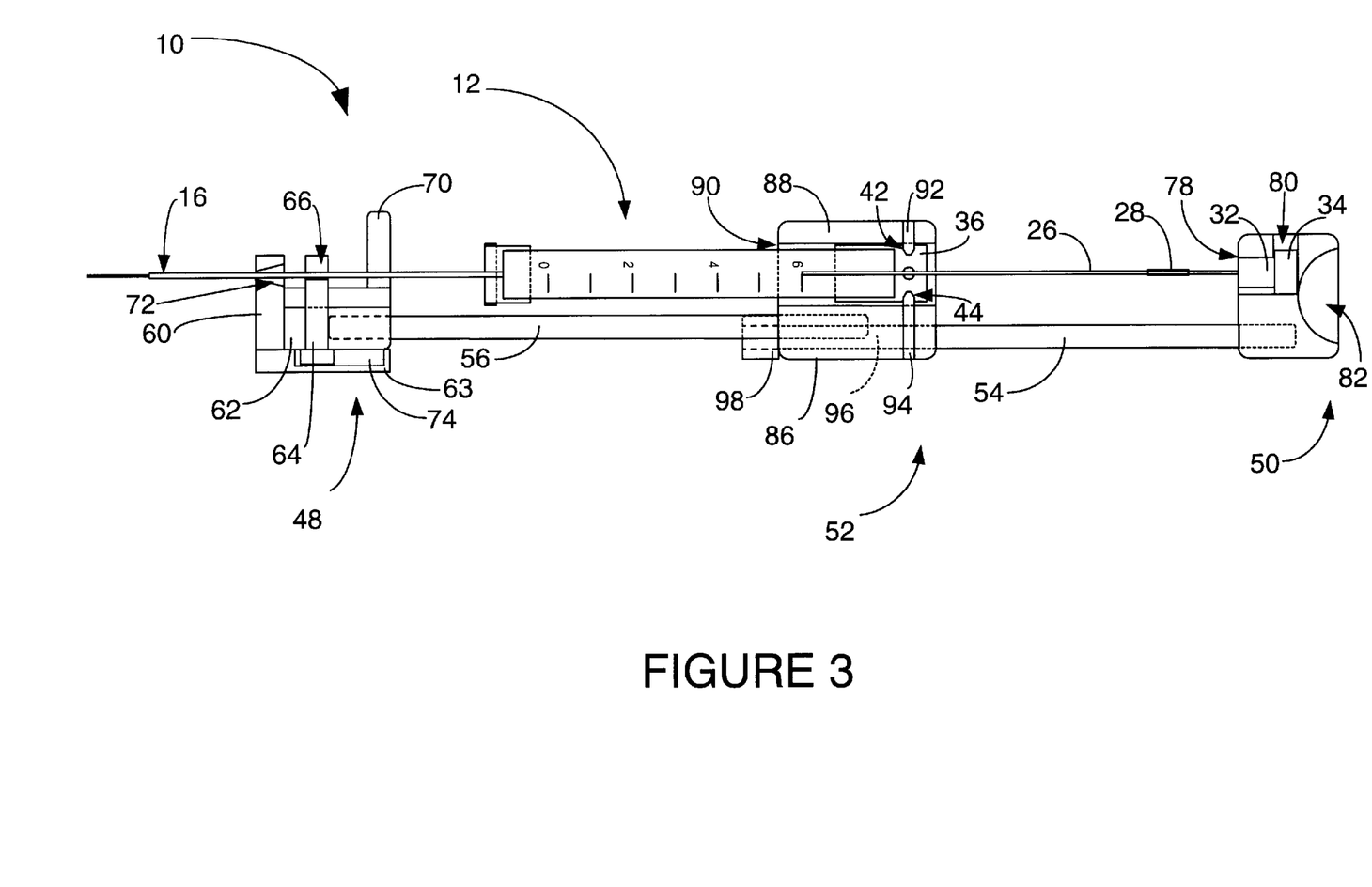
FIG. 3 illustrates a side cutaway view of the syringe array of the present invention as taken through line 3—3 in FIG. 2.

FIG. 3 shows a cut-away view of the syringe array 10 as taken through line 3—3 in FIG. 2. Line 3—3 is assumed to pass directly through the guide pins 64, and upper and lower pivot pins 92, 94.

In the proximal assembly 48, the footplate 60, slot plate 62, guide pin retainer 63, guide pin 64, guide slot 74 and control tab 70 can be seen. It can be seen how the needle 16 passes through the footplate transverse slots 72 and rests in the needle slot 66. In the preferred embodiment, the transverse slots 72 are tapered to allow easy replacement of syringe needles 16, as the tapering allows the needle 16 to be rotated up out of the needle slot 66.

In the pivot assembly 52, the syringe 12 with plunger cap 36, can be seen in the housing cavity 90, being held in place by the upper pivot pin 92 engaged in upper pivot hole 42, and lower pivot pin 94 engaged in lower pivot hole 44. The top cover 88 is shown holding the upper pivot pin 92 in place, while the pivot housing 86 holds the lower pivot pin 94. Also visible are the plunger 26 and the plunger enlarged portion 28.

In the distal assembly 50, the handle shaft 32 is placed in the handle slot 78, while the enlarged handle end 34 is captured by the transverse handle slot 80. A portion of the finger groove 82 is also visible.

Holding the assemblies together, a slide rod 54 can be seen passing through the through channel 96 with a retaining collar 98 at its end. Also illustrated is a stationary rod 56.

Figure 4:
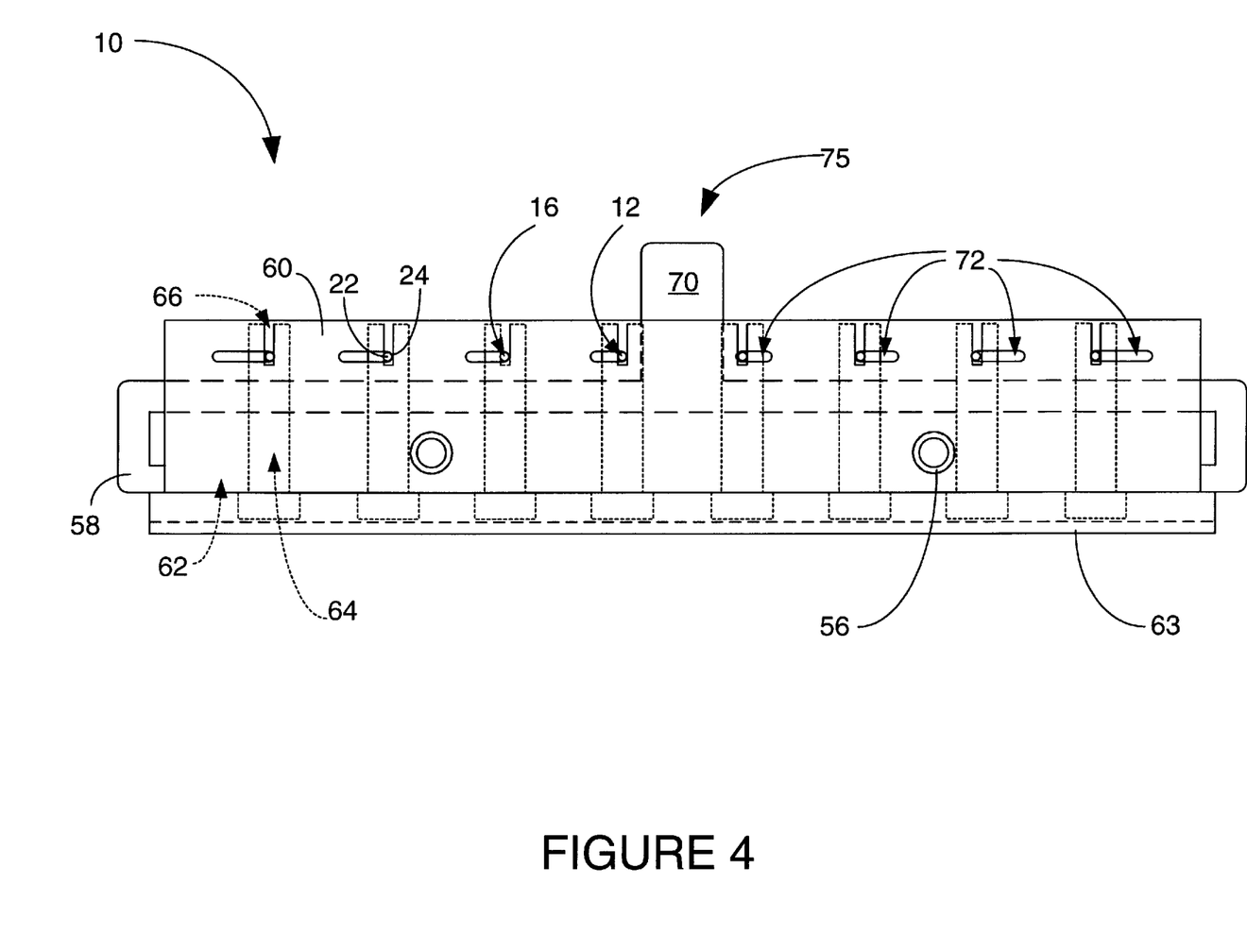
FIG. 4 shows a front side plan view of the syringe array of the present invention.

FIG. 4 shows an end view of the syringe array 10 with the proximal housing 58, footplate 60, control tab 70, guide pin retainer 63, and the ends of the stationary rods 56, as well as the ends of the needle inner members 22 and the needle sheaths 24. The guide pins 64, slot plate 62 and needle slots 66 are all shown in dashed lines. It can be seen how the needles 16 of the syringes 12 are held in the needle slots 66 of the guide pins 64, and then pass through the footplate transverse slots 72, where they are free to move laterally in response to changes in the needle spacing. Needle slots 66 allow easy replacement of syringe & syringe needles 16. Guide pin retainer 63 keeps guide pins 64 in place and allows guide pins 64 to move in guide slots 74. The guide pins 64 guide slots 74 and control tab 70 thus make up an adjusting portion 75 of the syringe array 10. This adjusting portion 75 is in this case shown to be in the proximal assembly 48. It is of course possible that the adjusting portion 75 could be located in the pivot assembly 52, as an alternative.

The transverse slots 72 shown in this figure are a series of separate slots of varying width which are useful in limiting the lateral travel of the needles 16. It should be understood that there could be many variations in the slots from the embodiment shown, and could, for example, be replaced with a single transverse slot extending from side to side and enclosing all 8 of the needles.

Figure 5:
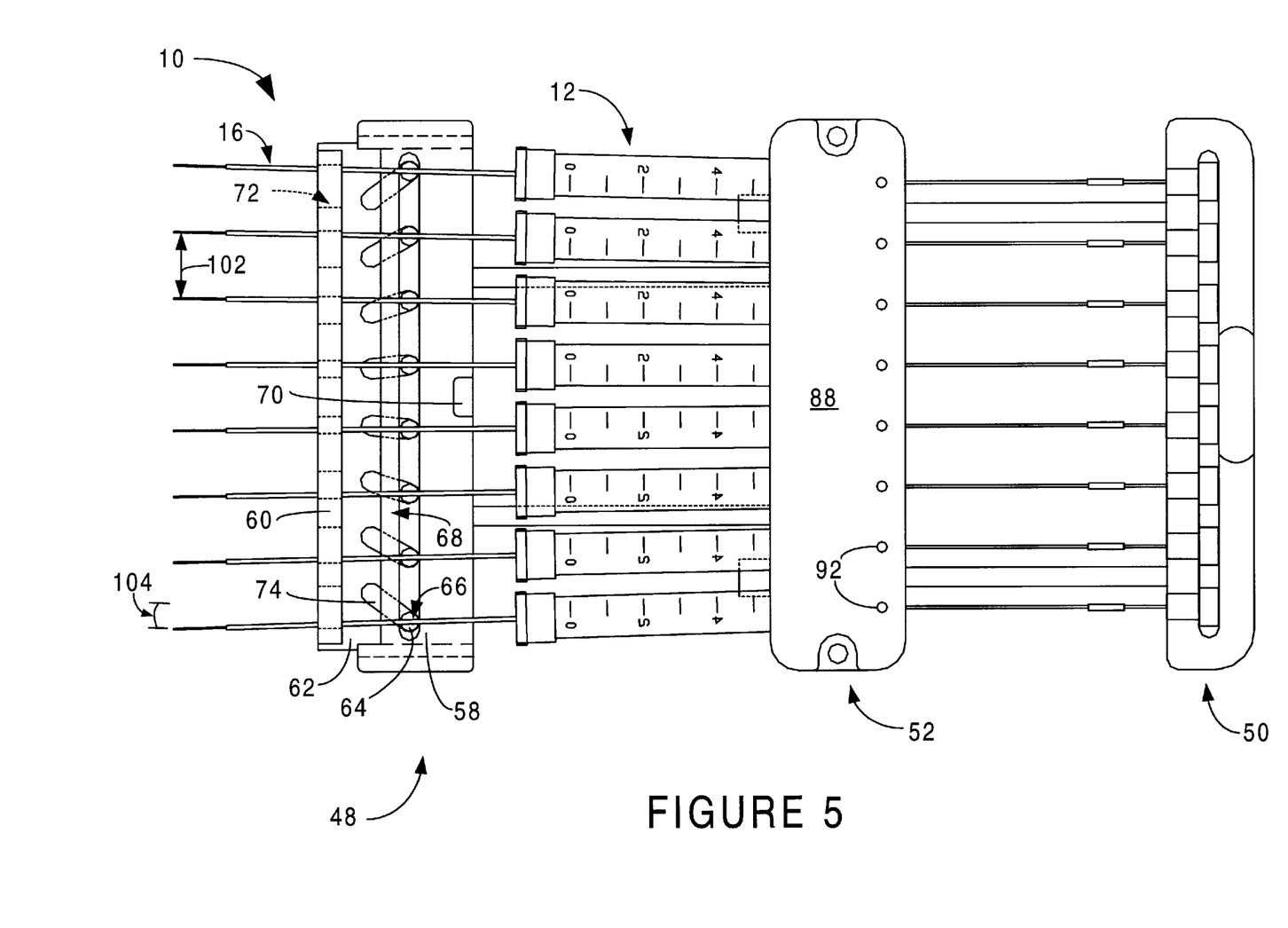
FIG. 5 illustrates a top plan view of the syringe array of the present invention, which is in the open and dispensing positions.

FIG. 5 illustrates a top plan view of the syringe array 10 in which the top cover 88 is still attached. The distal assembly 52 is again drawn back away from the pivot assembly 50, so that the device is in dispensing position. Now, however, the control tab 70 has been drawn in the distal direction so that the proximal housing 58 has pulled all the guide pins 66 to the distal ends of the guide slots 74 in the slot plate 62, and away from the footplate 60. The guide pins 66 thus slip toward the distal end of the needles 16 and move apart from each other in the proximal housing transverse slot 68. The needles 16 consequently spread apart in the transverse slots 72 and assume the open position, wherein the needle spacing 102 has been maximized.

As the tips of the needles 16 travel from a first, closed position having a closed position spacing 100 (FIG. 1) to a final open position spacing 102 (FIG. 2), the needle tips can be conceived of as traveling a path 104, shown exaggerated in FIG. 5. It is possible that the path be a smooth continuum from first spacing to a final spacing, with positioning anywhere in between. It is possible that the control tab be fitted with a pointer which could indicate spacings on a small chart to make adjustment easier. It is also possible that the path contain discrete stops which correspond to spacings used in various models of sequencers. The stops could be implemented by having the control tab 70 biased against a surface containing teeth or notches which would serve to establish the desired spacing dimensions. Thus although the preferred range of spacing for this device is presently 9.0 mm to 10.8 mm, these could be stops along a wider continuum of adjustment.

A typical operating situation for the syringe array 10 is for use in transferring micro-liter volumes of liquid from 96 well microplates with 9 mm center-to center spacing, or 384 well microplates with 4.5 mm spacing, to a sequencing gel for processing on an automated sequencer. Sequencing gels for automated sequencers are typically 0.2 mm or 0.4 mm thick. They are made of a porous matrix of cross-linked polymers sandwiched between two glass plates. The length and width of the gels can range in size up to approximately 30 cm×40 cm. The syringe array 10 has to be able to dispense samples so that they flow between the glass plates and onto the top of the gel which is about one centimeter below the top edges of the glass plates. The needles 22 are therefore necessarily of a very narrow gauge.

Sequencing gels can be configured for different numbers of "wells", each of which will hold a different sample. A well is essentially a chamber at the top surface of the gel where the surface of the gel is the well bottom and the sides of the well are formed by two "teeth" of a plastic "comb". A comb is inserted down between the plates until all the teeth contact the top of the gel and form the wells. The tops of the wells are open for samples to enter. For the ABI 377Automated Sequencer, which is typical of devices in the industry, the maximum number of wells has been 72. Recently ABI has introduced an upgrade to hardware and software that allows 96 samples (in 96 wells) to be run on a single gel. The different combs that form 64, 72, 96, etc. wells are all the same length but differ in their number of teeth contained in that length, and therefore the number of wells they will form. The width of the gel for a given automated sequencer stays the same so when there is an increase in the number of wells, the wells become more narrow. An important point is that by changing the width of the wells the center-to-center spacing of the wells is changed.

Most of the combs available conform to a "standard" center-to-center well spacing such that when the spacing is multiplied by 2, 3, 4, or 5 it equals 9 mm. A multi-channel loader with a fixed 9 mm spacing is able to aspirate 8 samples from a 96 well plate and dispense into every 2nd, 3rd, or 4th, etc. well of a sequencing gel made with a "standard" comb. In other words, 9 mm is the distance between the centers of wells 1 and 3, or 1 and 4, or 1 and 5. It is necessary to skip the intervening wells and come back with subsequent transfers to fill them and then have some algorithm set up to keep track of which sample is which.

The center-to-center spacing of the wells made with the new 96 well comb for the ABI377 automated sequencer is 1.8 mm. Since 1.8 mm×5=9.0 mm, one could load many (but not all) wells of a gel made with this comb using the 9.0 mm fixed spacing gel loaders now available on the market. The problem with the 9.0 mm fixed spacing loader is that after 10 transfers of eight samples each wells 1–80 are filled but wells 81–96 cannot be filled. The next transfer would try to fill wells 81, 86, 91, 96, 101, 106, 111, and 116 but would be beyond the right edge of the gel. The only way to fill all 96 wells with an eight channel loader is with 12 dispenses of every sixth well (1.8 mm×6=10.8 mm), 12 dispenses of every third well (1.8 mm×3=5.4), or by loading adjacent wells. The preferred embodiment is designed to expand from a 9.0 mm spacing of the needles to 10.8 mm spacing thereby allowing all 96 wells to be filled with 12 dispenses loading every sixth well. In the transfer of material from wells having smaller spacing to wells having larger spacing, the syringe array 10 will be adjusted so that the control tab 70 is pushed to the limit of the proximal direction and the array 10 is in closed position. The needle spacing 100 is thus preferably 9 mm, as in FIG. 1, to match the 9 mm center-to center spacing of the multi-well microplate from which material is to be collected. The distal assembly 50 will be initially pressed to the limit of travel in the proximal direction so that the array 10 is in aspirating position. After the needle tips 22 are inserted in the wells of the material to be transferred, the distal assembly 50 is then drawn in the distal direction so that all eight plungers are simultaneously withdrawn to collect the material in the syringes 12.

When dispensing material to a sequencing gel where a center-to-center spacing of 10.8 mm is desirable, the control tab is pulled to the limit of travel in the distal direction, thus expanding the needle spacing 102 to the open position, as seen in FIG. 5. The material is then dispensed by moving the distal assembly 50 in the proximal direction, thus pressing all the plungers 18 simultaneously to place material in the wells of the gel.

The transfers just described assume going from lesser to greater spacings but the reverse would be possible as well. It is also possible to use other ranges of spacings than from 9 mm to 10.8 mm. It is possible that 9 mm and 10.8 mm are stops in a larger range of spacings, and there may be an additional mechanism included in the syringe array that has notches or indicator settings to mark the more commonly used spacings. For example, the control tab could be spring biased to fit in a series of notches as it is drawn further into a wider and wider open position, one of which notches corresponds to 9 mm spacing and other which could be for 10.8 mm spacing. Any number of such mechanisms will be obvious to one skilled in the art, and are included in the true spirit and complete scope of the present invention. It is also possible the spacing could be 9 mm to 4.5 mm for 96-well to 384-well transfers or 2.25 mm for 1536-well transfers. Other spacings could be used for transfers from 384-well or 1536-well plates to gel loaders of various well-to-well spacing.

In addition to the above mentioned examples, various other modifications and alterations of the inventive device 10 may be made without departing from the invention.

INDUSTRIAL APPLICABILITY

The present syringe array with adjustable needle spacing 10 is well suited for many laboratory applications. In particular, for applications where multiple wells of a gel sequencer are being loaded, the present invention will be very useful.

ABI 377Automated Sequencer, which is typical of devices in the industry, has used 72 well format. Recently ABI has introduced an upgrade to hardware and software that allows 96 samples (in 96 wells) to be run on a single gel. This of course, allows a greater number of samples to be run simultaneously in the same period of time. In order for laboratory personnel to take advantage of this opportunity for increased efficiency, it is important that materials handling apparatus be compatible with these new advances. To be able to interface with the changed center-to-center spacing of these newer sequencers, the present invention 10 allows the needle spacing to be adjusted. Without this capability, laboratory personnel must purchase new syringe arrays to match the sequencer in use. Worse yet, in a lab which may have a variety of sequencers, some new, some old, each with differing well spacings, it would be necessary to assign a dedicated set of syringe arrays with compatible needle spacings to each machine.

By having adjustable needle spacing, dedicated syringe array sets are not necessary. It is not necessary to remember which set matches with which sequencer. Also it enables personnel to use a number of different sequencers at one time. An adjustable syringe array can be filled with material to be dispensed, a gel in one sequencer with one spacing requirement can be filled, and then a gel in a second machine with a second spacing requirement may be filled from the same syringe array after adjustment, perhaps without reloading the array.

Ordering new arrays is much easier if one array model can be purchased, rather than a myriad of differing models. Processing in general is expedited. Innovation in sequencer efficiency design may be encouraged because further increase in the number of wells per gel may be accommodated by adjusting the needle spacing to fit. Innovation may not be hampered by the concern that customers will have to discard their old material handling equipment and by new ones in order to be compatible.

For the above, and other, reasons, it is expected that the syringe array with adjustable needle spacing 10 of the present invention will have widespread industrial applicability. Therefore, it is expected that the commercial utility of the present invention will be extensive and long lasting.

What is claimed is:

1. A syringe array for holding a plurality of syringes, each syringe having a barrel, a plunger located at the syringe's distal end, and a needle located at the syringe's proximal end, comprising:

a distal assembly wherein each plunger of said plurality of syringes is held, and by which all of the plurality of plungers are urged to move in unison;

a pivot assembly wherein a portion of each said barrel of said plurality of syringes is pivotally attached to a pivot; and a proximal assembly wherein each needle of said plurality of syringes is positioned with a controlled center-to-center spacing from each other, wherein;

an adjusting portion of said syringe array is adjustable to controllably change said needle center-to-center spacing from a first spacing to at least a second spacing as said barrel portions are allowed to rotate about said pivots.

2. A syringe array as in claim 1, wherein:

said adjusting portion of said syringe array is within said proximal assembly.

3. A syringe array as in claim 2, wherein:

said proximal assembly includes a plurality of guide pins which slidably capture and direct said needles, said guide pins being confined to travel in at least one slot in a slot plate, said at least one slot being configured so that said guide pins spread apart from each other as they travel, thus changing said needle center-to-center spacing from a first spacing to at least a second spacing.

4. A syringe array as in claim 1, wherein:

said adjusting portion moves said needle center-to-center spacing along a path from a first spacing to a final spacing.

5. A syringe array as in claim 4, wherein:

said center-to-center spacing path from first spacing to final spacing is a smooth and continuous path whereby said center-to-center spacing is adjustable to any spacing along a continuum from first spacing to final spacing.

6. A syringe array as in claim 4, wherein:

said center-to-center spacing path from first spacing to final spacing include a plurality of discrete stops, corresponding to spacings useful for specific applications.

7. A syringe array as in claim 4, wherein:

said first spacing is 9.0 mm and said final spacing is 10.8 mm.

8. A syringe array as in claim 1, wherein:

the number of syringes in said plurality of syringes is chosen from the set consisting of 4, 6, 8, 10, and 12 syringes.

9. A syringe array as in claim 1, wherein:

said pivots of said pivot assembly are attached to the distal end of said syringe barrels.

10. A syringe array as in claim 1, wherein:

said pivots of said pivot assembly are attached to the proximal end of said syringe barrels.

* * * * *